(12) United States Patent
Eckert et al.

(10) Patent No.: US 11,672,879 B2
(45) Date of Patent: Jun. 13, 2023

(54) MAGNETIC LATCH CONNECTOR ASSEMBLY

(71) Applicant: CHISCAN HOLDINGS, LLC, Las Vegas, NV (US)

(72) Inventors: Bryon K. Eckert, Tempe, AZ (US); Bradley N. Eckert, Tempe, AZ (US); Huan Truong, Tempe, AZ (US)

(73) Assignee: CHISCAN HOLDINGS PTE. LTD., Parkview Square (SG)

( * ) Notice: Subject to any disclaimer, the term of this patent is extended or adjusted under 35 U.S.C. 154(b) by 463 days.

(21) Appl. No.: 16/641,615

(22) PCT Filed: Aug. 23, 2018

(86) PCT No.: PCT/US2018/047800
§ 371 (c)(1),
(2) Date: Feb. 24, 2020

(87) PCT Pub. No.: WO2019/040778
PCT Pub. Date: Feb. 28, 2019

(65) Prior Publication Data
US 2021/0128765 A1    May 6, 2021

Related U.S. Application Data

(60) Provisional application No. 62/549,351, filed on Aug. 23, 2017.

(51) Int. Cl.
*A61L 2/14* (2006.01)
*A61B 90/80* (2016.01)
(Continued)

(52) U.S. Cl.
CPC ............... *A61L 2/14* (2013.01); *A61B 90/80* (2016.02); *H05H 1/48* (2013.01);
(Continued)

(58) Field of Classification Search
CPC ...... A61L 2/14; A61L 2/0011; A61L 2202/16; A61B 90/80; A61B 2018/00732;
(Continued)

(56) References Cited

U.S. PATENT DOCUMENTS

| 9,656,095 B2 | 5/2017 | Watson et al. | |
| 2009/0066256 A1* | 3/2009 | Stone | B64G 1/40 |
| | | | 315/111.21 |

(Continued)

FOREIGN PATENT DOCUMENTS

WO    WO 2009/069117    *    6/2009

OTHER PUBLICATIONS

International Preliminary Report issued in International Application No. PCT/US18/47800, dated Mar. 5, 2020, 6 pages.
(Continued)

*Primary Examiner* — Xiuyu Tai
(74) *Attorney, Agent, or Firm* — Messner Reeves LLP

(57) ABSTRACT

A connector is configured to electrically connect a plasma emitter array with an identification chip to a power supply controller, and to further mechanically support the emitter device supporting the array during use. Cooperating components of the connector and emitter device form a magnetic latch assembly: the connector includes one or more magnets flush with a top receiving surface of the connector, and one or more alignment pegs extending outward from the receiving surface; the emitter device includes a steel plate attached to a substrate, and one or more holes disposed through the plate and the substrate. The holes align with the alignment pegs and the magnets attract the plate and secure the emitter device against the top receiving surface. Electrical contacts of the connector establish electrical communication with the
(Continued)

identification chip, providing power to the emitter device and enabling the controller to read data stored in the identification chip.

14 Claims, 9 Drawing Sheets

(51) Int. Cl.
  *H05H 1/48* (2006.01)
  *H05H 1/24* (2006.01)
  *A61B 18/00* (2006.01)
(52) U.S. Cl.
  CPC ...... *A61B 2018/00732* (2013.01); *H05H 1/47* (2021.05); *H05H 2240/20* (2013.01); *H05H 2245/30* (2021.05)
(58) Field of Classification Search
  CPC ........ A61B 18/042; A61B 2018/00452; H05H 1/48; H05H 2245/30; H05H 1/47; H05H 2240/20; H05H 1/2406; H05H 2277/10; H05H 2245/60; H05H 1/2425; H05H 1/2418; A61N 1/44; A61M 2207/00; A61M 35/10
  See application file for complete search history.

(56) References Cited

U.S. PATENT DOCUMENTS

| 2017/0094769 A1 | 3/2017 | Eckert et al. |
| 2017/0128117 A1 | 5/2017 | Myers et al. |

OTHER PUBLICATIONS

International Search report and Written Opinion issued in International Application No. PCT/US18/47800, dated Oct. 22, 2018, 6 pages.

\* cited by examiner

MAGNETIC LATCH CONNECTOR ASSEMBLY

CROSS-REFERENCE TO RELATED APPLICATIONS

This application is a U.S. National Stage of PCT Application No. PCT/US2018/047800 filed on Aug. 23, 2018 which claims the benefit of U.S. Provisional Patent Application No. 62/549,351, filed under the same title on Aug. 23, 2017, and incorporated fully herein by reference.

FIELD OF INVENTION

The present invention relates to a device used to drive non-thermal plasma emitters and control the emitted plasma for use in plasma medicine including therapeutic and diagnostic applications.

BACKGROUND

Plasma is an ionized state of matter known for its cleaning, decontaminating, sterilizing, antimicrobial, and healing properties when applied to an inanimate surface or to tissue. Plasma can be created when energy is applied to a substance. As energy input is increased the state of matter changes from solid, to liquid, to a gaseous state. If additional energy is fed into the gaseous state, the atoms or molecules in the gas will ionize and change into the energy-rich plasma state, or the fourth fundamental state of matter.

There are two types of plasma, thermal and non-thermal, which is also known as cold plasma. Thermal plasmas are in thermal equilibrium, i.e. the electrons and the heavy particles are at the same temperature. Current technologies create thermal plasma by heating gas or subjecting the gas to a strong electromagnetic field applied with a generator. As energy is applied with heat or electromagnetic field, the number of electrons can either decrease or increase, creating positively or negatively charged particles called ions. Thermal plasma can be produced by plasma torches or in high-pressure discharges. If thermal plasma is used in treating a material or surface sensitive to heat, it can cause significant thermal desiccation, burning, scarring and other damage.

In order to mitigate such damage, methods and devices have been created for applying non-thermal plasma to heat-sensitive materials and surfaces. Whereas in thermal plasmas the heavy particles and electrons are in thermal equilibrium with each other, in non-thermal plasmas the ions and neutrals are at a much lower temperature (sometimes as low as room temperature) than the electrons. Non-thermal plasma usually can operate at less than 104.degree. F. at the point of contact. Thus non-thermal plasmas are not likely to damage human tissue.

To create non-thermal plasma, a potential gradient is applied between two electrodes. Typically the electrodes are in an environment of a fluid such as helium, nitrogen, heliox, argon, or air. High voltage is applied between the two electrodes and a gas mixture, such as helium and oxygen, is flowed through the holes of the electrodes. When the potential gradient is large enough, a plasma is ignited in the gap between the electrodes and a plasma plume discharged through the aperture of the outer electrode and into the surrounding room air. The plume can be used to treat surfaces by scanning it across the surface.

Some non-thermal plasma generation systems require a source of forced (i.e., pressurized) gas to drive the plasma emitters. Such systems can be very large and cumbersome, requiring the use of gas tanks to supply the necessary fluid to create the plasma. Another disadvantage is that there is only a narrow contact point between the plasma plume and the surface that it comes into contact with. Typically, plumes are usually on the order of 1 cm in diameter. This makes treating larger areas time-consuming and tedious, since the contact point has to be moved back and forth across the area to be treated. The uniformity of treatment across the treatment area may be difficult to control.

The application of non-thermal plasma in medical, therapeutic, and cosmetic modalities has recently been a fruitful field of research. The beneficial health effects of non-thermal plasma applications in living organisms are often attributed to reactive oxygen or nitrogen species. Non-thermal plasma may be placed in contact with an affected area of the skin or body in order to produced healthful benefits. These benefits can be realized or enhanced by applying the non-thermal plasma according to a treatment protocol designed to treat a particular malady or produce a particular benefit; such protocols, which may specify parameters such as current amplitude, modulation of the plasma at certain frequencies, and duration and repetition of treatment, continue to be developed as new and refined applications are researched.

DETAILED DESCRIPTION

Non-thermal plasmas occur when the electrons are in a much more energetic state than the neutral or positively charged particles. The application of non-thermal plasma to biological specimens has recently been an area of increasing interest. Numerous published papers have noted positive biological effects imparted by non-thermal air plasma. The health effects observed in living organisms are often attributed to reactive oxygen or nitrogen species produced as byproducts of the plasma generation. A closer investigation of the effects imparted by an array of micro-plasmas placed near the skin shows that the parameters of the plasma application, such as modulation frequency, duration, or area of application may be important for different therapeutic benefits. Furthermore, specific modulation frequencies have been correlated with the killing of specific microorganisms, including forms of bacteria, virus, fungus, and mold.

One application of plasma utilizes an array of non-thermal air plasma plumes. A non-thermal plasma device may have a plurality of plasma emitting electrodes disposed on a rigid or semi-rigid substrate of an appropriate size or shape for the target area. The array of electrodes can be used to apply non-thermal plasma treatments in a uniform manner to a specific treatment area. The array may be driven by a power supply that operates at high voltage, and a controller for precisely emitting plasma at desired frequencies and power levels based on the type and area of treatment. The array may be consumable/disposable, as described below, while the controller and power supply generally are not; an interface between the array and the controller/power supply that allows the array to be disconnected and replaced is needed. This invention provides a quick connect interface between a plasma array and a power supply controller, using a magnetic latch to secure the array to the connector and seat corresponding sets of electrical contacts on the connector and the array in communication with each other. The connector may have an interlock mechanism that prevents incorrect attachment of an array and other unsafe usage of the plasma device. Further, through the connector's electrical contacts, the controller can read data stored on the array to identify important metadata about the array being used and provide customization features such as preprogrammed protocols, use limitations, and array verification.

Figure 1A:
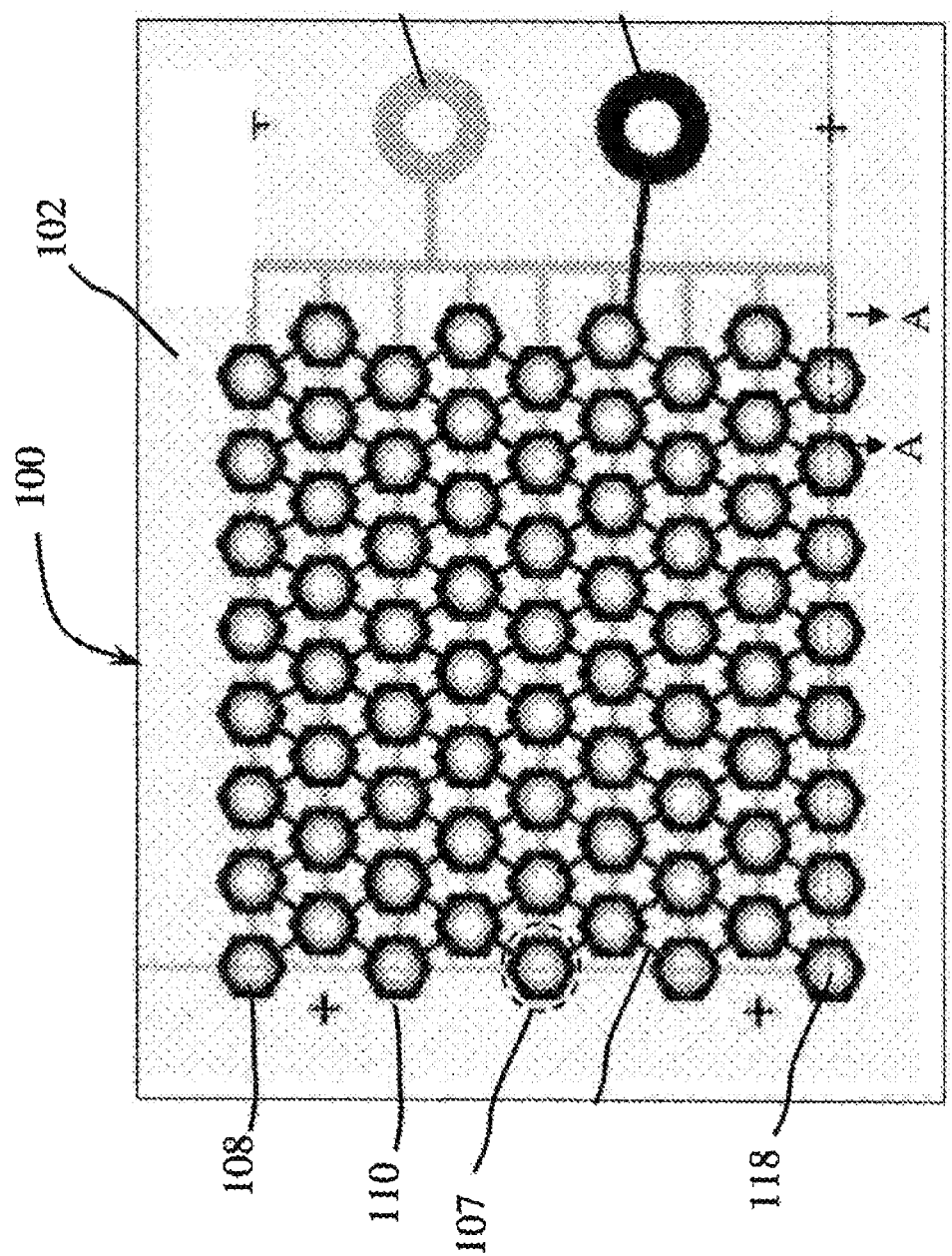
FIG. 1A is a top view of a plasma array emitter.
Figure 1B:
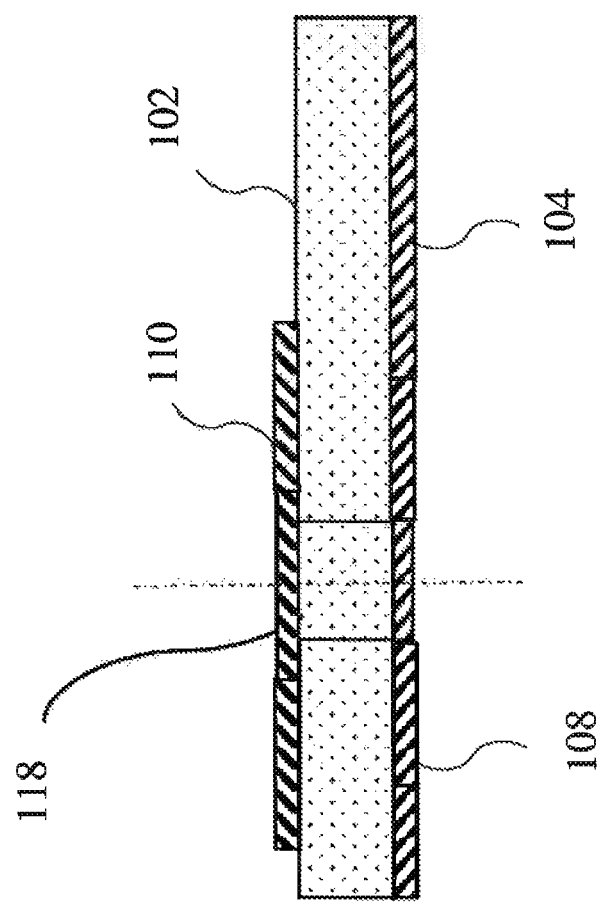
FIG. 1B is a cross-sectional partial side view of the plasma array emitter of FIG. 1A.

Referring to FIGS. 1A and 1B, an example array 100 comprises a substrate 102 having at least two opposing surfaces, referred to herein sometimes as a top and bottom for convenience. A plurality of through-holes 118 are made in the substrate 102. A plurality of drive electrodes 110 are placed on the top of the substrate 102, with each drive electrode 110 centered over one through-hole 118 in the substrate 102. A plurality of ground electrodes 108 is placed on the bottom of the substrate 102, with each ground electrode 108 centered over one through-hole 118 in the substrate 102. The resulting structure of a through-hole 118, a ground electrode 108, and a drive electrode 110 comprises a plasma emitter 107. The emitters 107 are arranged such that when the array 100 is connected to a voltage source the emitters generate a plurality of non-thermal plasma corona discharges. The discharges generate ionized gas, which in turn creates reactive species including ozone and nitric oxide.

The substrate 102 is typically made of a dielectric material such as alumina, polycarbonate, polyimide, polyester, polytetrafluoroethylene-infused woven glass cloth, polypropylene, glass-reinforced epoxy laminate sheets, or similar. In certain embodiments a substrate may have more than one layer, and the layers may be made of different materials. The substrate 102 can be made of a rigid or a flexible material that can be made to conform to varying surface topography and shapes such as a rough, textured, or a smooth surface. The substrate can be two-dimensional, such as a square, curved, rectangular, round, or hexagonal. It can also be three-dimensional such as curved, cubic, tubular, or spherical. The substrate may also have a non-uniform shape or a non-symmetric shape. Substrates of rigid materials may be shaped to the desired conformation before or after the plasma emitters are made therein. Substrates of flexible materials are typically conformed to the desired shape after the array is manufactured.

Using mass manufacturing techniques, the cost of making the arrays is small enough that the arrays can generally be considered consumable or disposable, simply thrown away or recycled after one or a few uses. Any polymer in the array is consumed by the oxygen plasma, in a process commonly known as ashing. This erosion process can be slowed by adding a thin layer of glass on top of the entire array. A sol-gel process can be used to deposit a layer of desired thickness, on the order of about a 100 nm. A thinner crystalline layer of $SiO_2$, $Al_2O_3$ or $Y_2O_3$ works too, and may be deposited by atomic layer deposition or plasma assisted atomic layer deposition, optionally after array burn-in for uniform plasma. These methods may cause an increase in manufacturing complexity and cost, and ultimately only slow the effects of ashing rather than preventing it outright. The non-thermal plasma array may inherently have a limited therapeutic lifetime due to the degradation of the polymer material, the potentially custom shapes or sizes used for different therapeutic protocols, length of plasma therapy treatments, or other factors.

To create the plasma, a high voltage is applied to one or more drive electrodes 110 on the substrate 102. The voltage may be supplied by a power supply, sometimes also referred to herein as a driver. It creates a high voltage at a high frequency. With the drive electrodes 110 at a high potential relative to the ground electrode 108, current flows through the drive electrodes 110 and through a fluid in the through-hole 118 and around the array. The fluid is ionized to create a plasma region around each drive electrode 110, ground electrode 108, or both. The ions from the ionized fluid pass a charge to a plurality of ground electrodes 108 or to an area of lower potential. In a preferred embodiment the power supply drives and controls an array 100 of non-thermal plasma emitters at desired frequencies at a controlled power level. The power supply controls the functionality of the array 100 such as time on/off, strength of plasma, strength of a plasma field from electrode to electrode, frequency, power level, and other similar parameters.

In addition to causing generation of the non-thermal plasma, it is desirable for the power supply controller to be able to control the plasma so that it can be used for beneficial purposes. Such parameters that must be controlled include the length of time the plasma is generated, the power level of the plasma, and frequency modulation and wave form of the plasma. Specific modulation frequencies are correlated to the killing of specific microorganisms, including forms of bacteria, virus, fungus, and mold. Therefore controlling such parameters is important to produce biological effects beyond those produced by the reactive species ozone and nitric oxide. To ensure the emitted plasma meets desired parameters and a user of the plasma device is following the proper protocol, it would be useful to limit the emissions to the desired parameters and by authorized persons. For example, a prescribed treatment protocol provided by a physician, pharmacist, or clinician, much like a conventional prescription for medicines used with other drug delivery devices, may be encoded into machine-readable data accessible by the controller, and the controller may be programmed to execute the protocol (and to otherwise prevent use of the device, in some embodiments). In another example, the array may have an ID chip or another identifying device that the controller may be programmed to process in order to confirm that the array is a valid array (e.g., the array meets a certification standard, or bears a manufacturer's watermark, or is associated with the user or the user's physician).

Figure 2A:
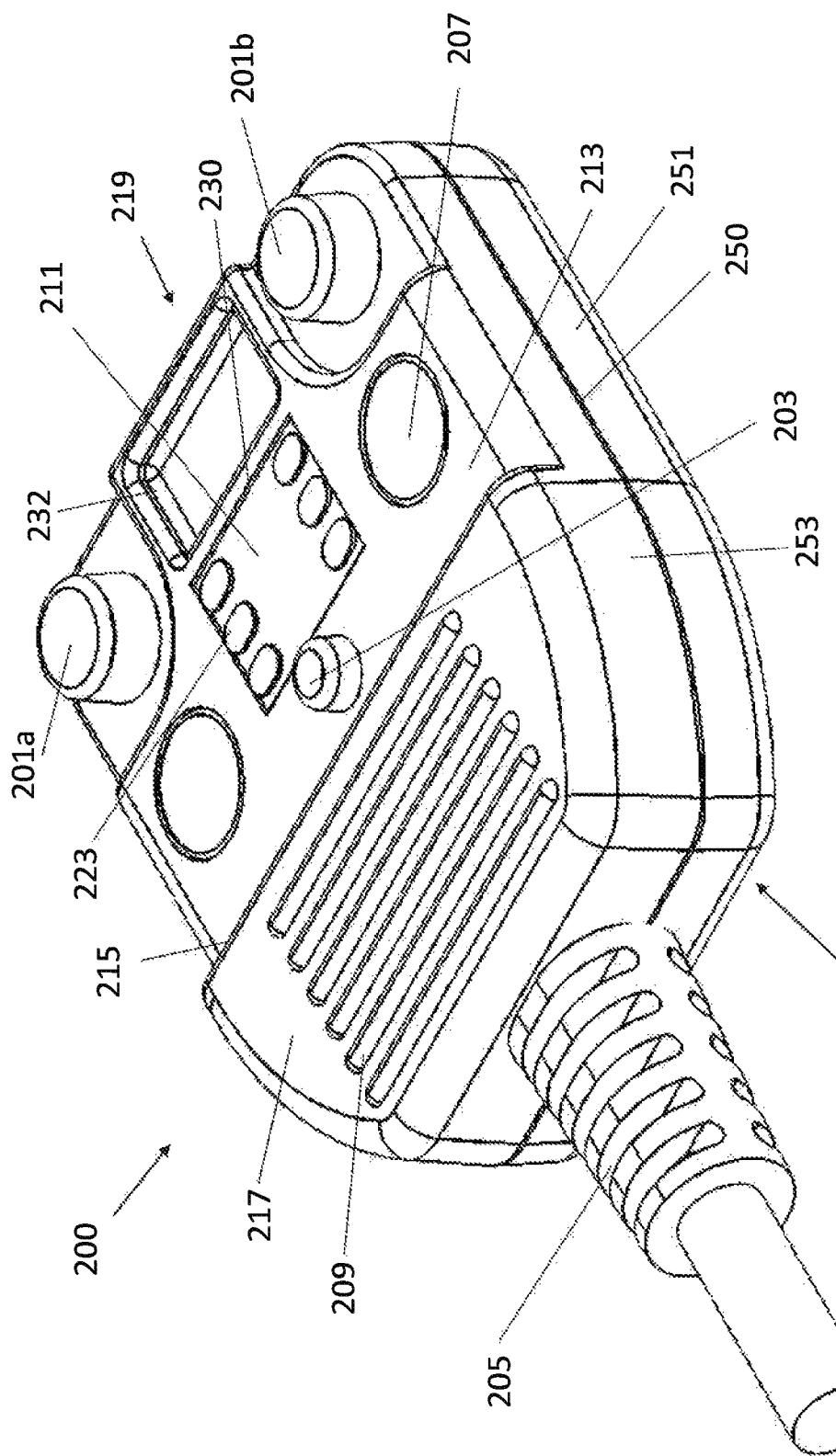
FIG. 2A is an isometric top-rear view of an example connector implementing a magnetic latch assembly in accordance with the present disclosure.
Figure 2B:
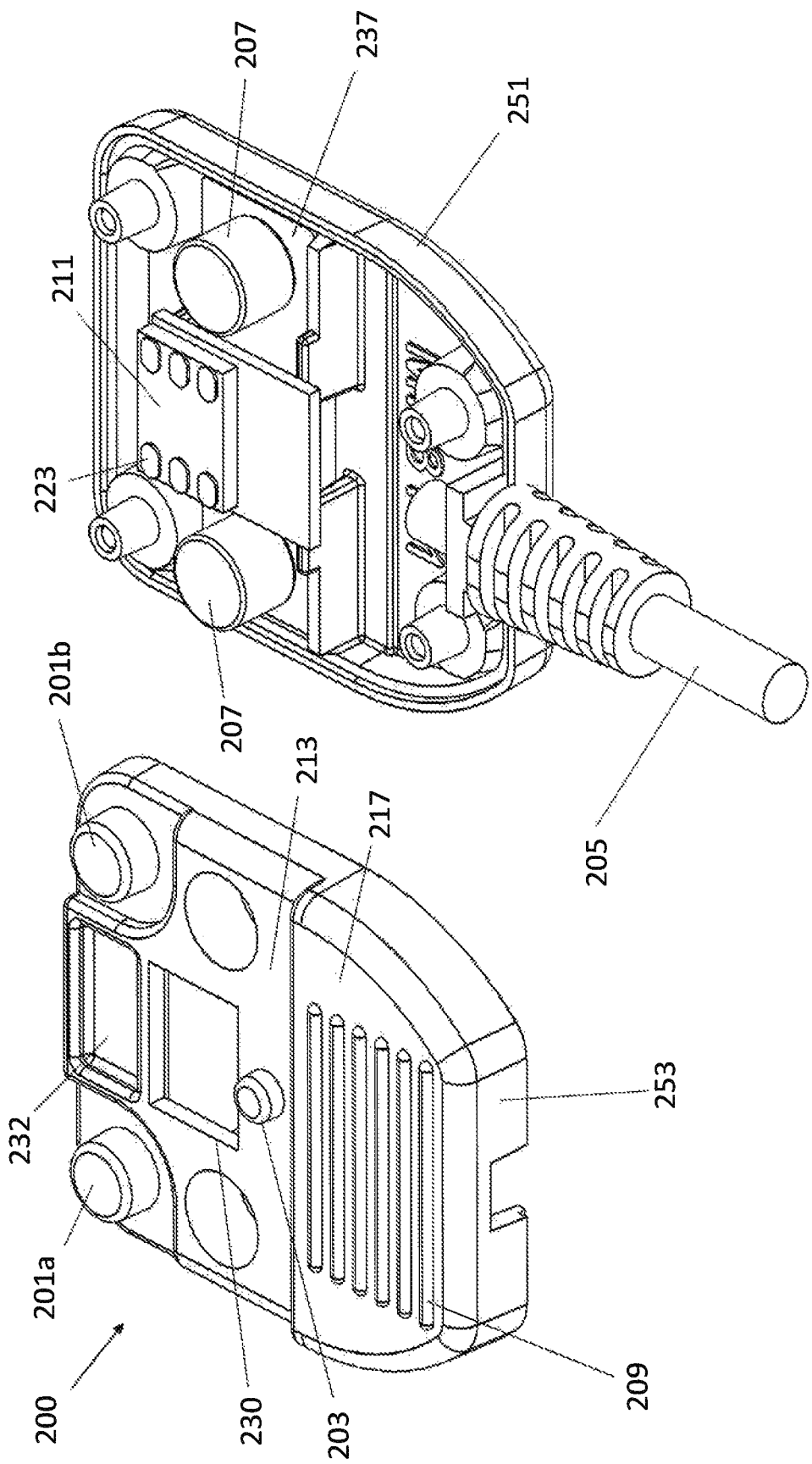
FIG. 2B is an exploded isometric top-rear view of the connector of FIG. 2A.
Figure 2C:
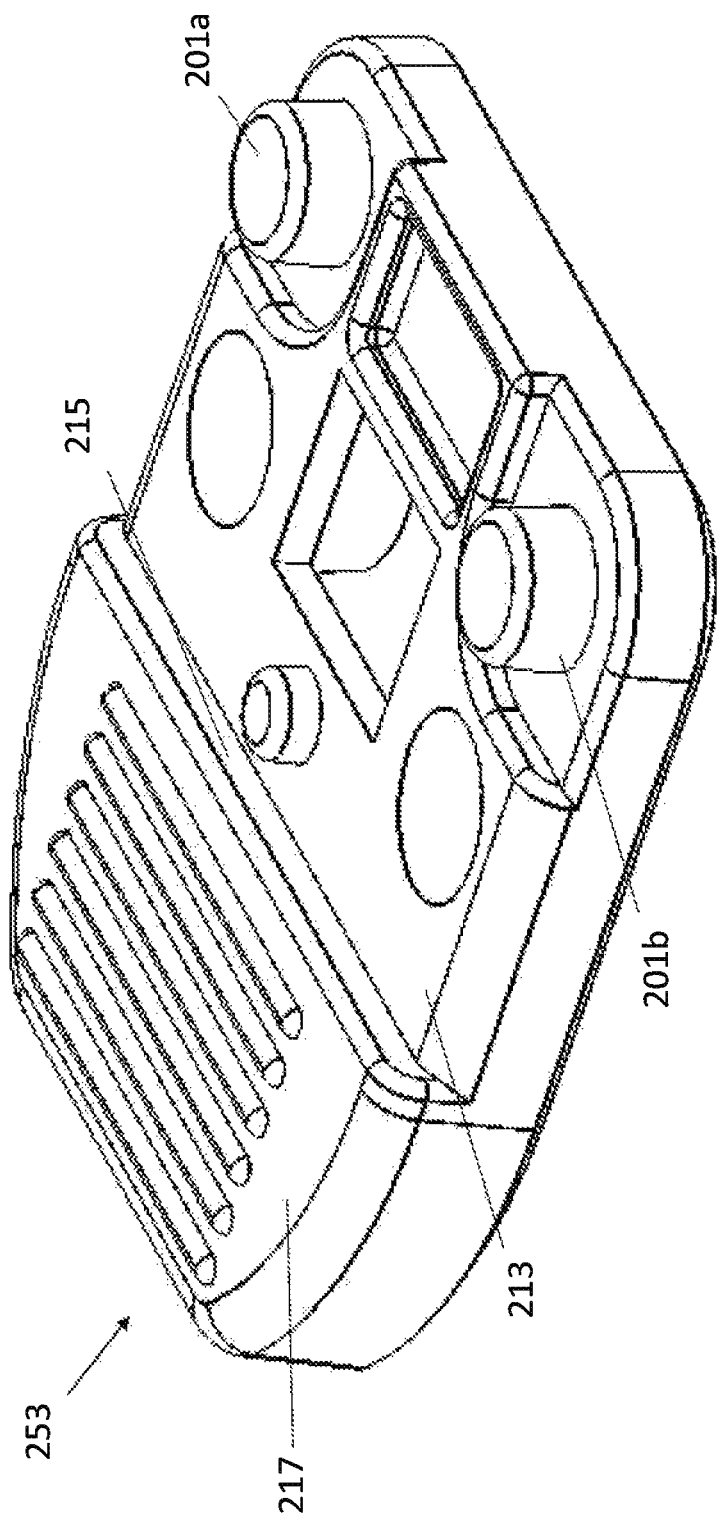
FIG. 2C is an isometric top-front view of a top half of the connector of FIG. 2A.

Referring to FIGS. 2A-C, a magnetic latch connector assembly, or "connector" 200, provides mechanical and electrical interfaces between a power supply/controller and a removable plasma array of a non-thermal plasma device. In various embodiments, the power supply and/or controller is connected by wire (i.e., electric cable 205) or wirelessly to the magnetic latch connector assembly, which serves as a quick-connect system for connecting plasma arrays to the power supply. FIGS. 2A and 2B illustrate an isometric view showing the top, rear, and side of an example embodiment of one portion of the connector 200. Connector 200 may include a hollow casing that encloses an interior space for housing electronic and magnetic components. The casing may be a plastic or similar material, and in some embodiments may be a 3D-printed polymer. In one embodiment a lower piece 251 and upper piece 253 may be joined along a seam 250 to form the casing of the connector 200. Fasteners or an adhesive may secure the lower piece 251 and upper piece 253 together. Planar face 213 and planar face 217 on the top of connector 200 are parallel but not coplanar, being separated by a small perpendicular distance forming face 215. Face 215 serves to divide the connector into a front section 219 and a thicker rear section 221. FIG. 2C is an alternate view of the upper piece 253 of connector 200, more clearly depicting planar face 215. Connector 200 is configured to receive a planar face of a plasma emitter array, with one face of the array lying coincident to face 213 and a bottom edge of the array coincident with planar face 215, as shown further below. The connector 200 may further include other faces and structures that facilitate connection and/or retention of various components of the connector 200 and/or a plasma emitter array. For example, an aperture 230 and a recess 232 may be formed into face 213; the aperture 230 may receive a chip reader 211 as described below, and the recess 232 may be positioned (i.e., proximally from the aperture 230) to receive a memory chip attached to and projecting from the interfacing surface of the plasma emitter array.

Referring back to FIG. 2A, three alignment pegs 201a, 201b, 203 extend upward from planar face 213 to lie coplanar with face 217 of connector 200. Pegs 201a, 201b, 203 align the connector with a plasma emitter array, to be described in more detail below. In some embodiments, pegs 201a and 201b may have a different circumference to ensure proper array orientation on the connector. Two neodymium magnets 207 are fastened within the enclosed space (not shown) of the connector 200. In some embodiments, the magnets 207 may be attached by epoxy or another suitable adhesive; additionally or alternatively, the magnets 207 may be built to a custom shape so as to be held in place (i.e., via friction fit or overmolding) by plastic receiving structures of the connector 200. Appropriately sized holes in planar face 213 expose a top surface of each magnet 207, the top surface being coplanar with face 213. At the respective top surfaces, the magnets 207 engage a magnetic surface of the plasma array to secure the array to the connector 200. An electronic chip reader 211, which will be described in further detail below, is positioned in connector 200. In some embodiments, electronic chip reader 211 may include spring socket electrical contacts 223 that extend slightly upward above face 213 and, when a plasma array is attached to the connector 200, bias against cooperating electrical contacts of the plasma array. An electronic cable 205 connected to electronic chip reader 211 within the enclosed area extends from connector 200 and attaches to a plasma power supply. A conductive solid or threaded core of the cable 205 may electrically connect to the contacts 223, completing the electrical communication path from the controller/power supply through the contacts 223 to the connected plasma array. A series of ridges 209 extend upward from face 217 a short distance, creating a textured area on the rear 221 of the connector 200 to facilitate gripping of the connector 200.

Within the enclosed space of connector 200 is a steel pole plate 237 (see FIGS. 2B and 5) that is attached to an interior bottom surface. The pole plate 237 circulates the magnetic flux so as to increase the magnetic pull of the latch. The pole plate 237 also keeps the magnetic field self-contained to ensure the magnetic field doesn't interfere with the plasma generation or modulation.

Figure 3B:
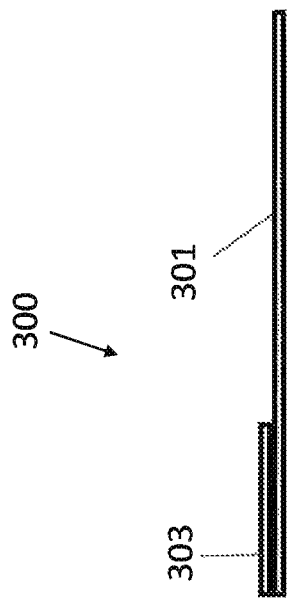
FIG. 3B is a left side view of the plasma emitter device of FIG. 3A.
Figure 3A:
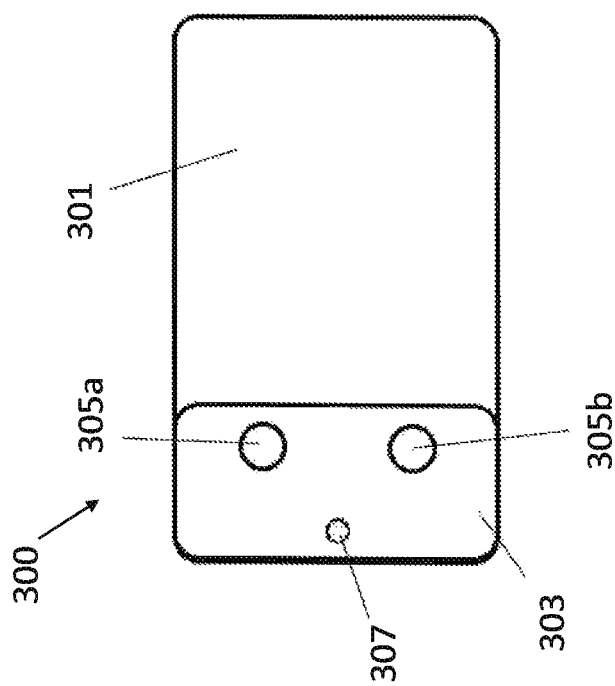
FIG. 3A is a top view of an example plasma emitter device implementing a magnetic latch assembly in accordance with the present disclosure.
Figure 3C:
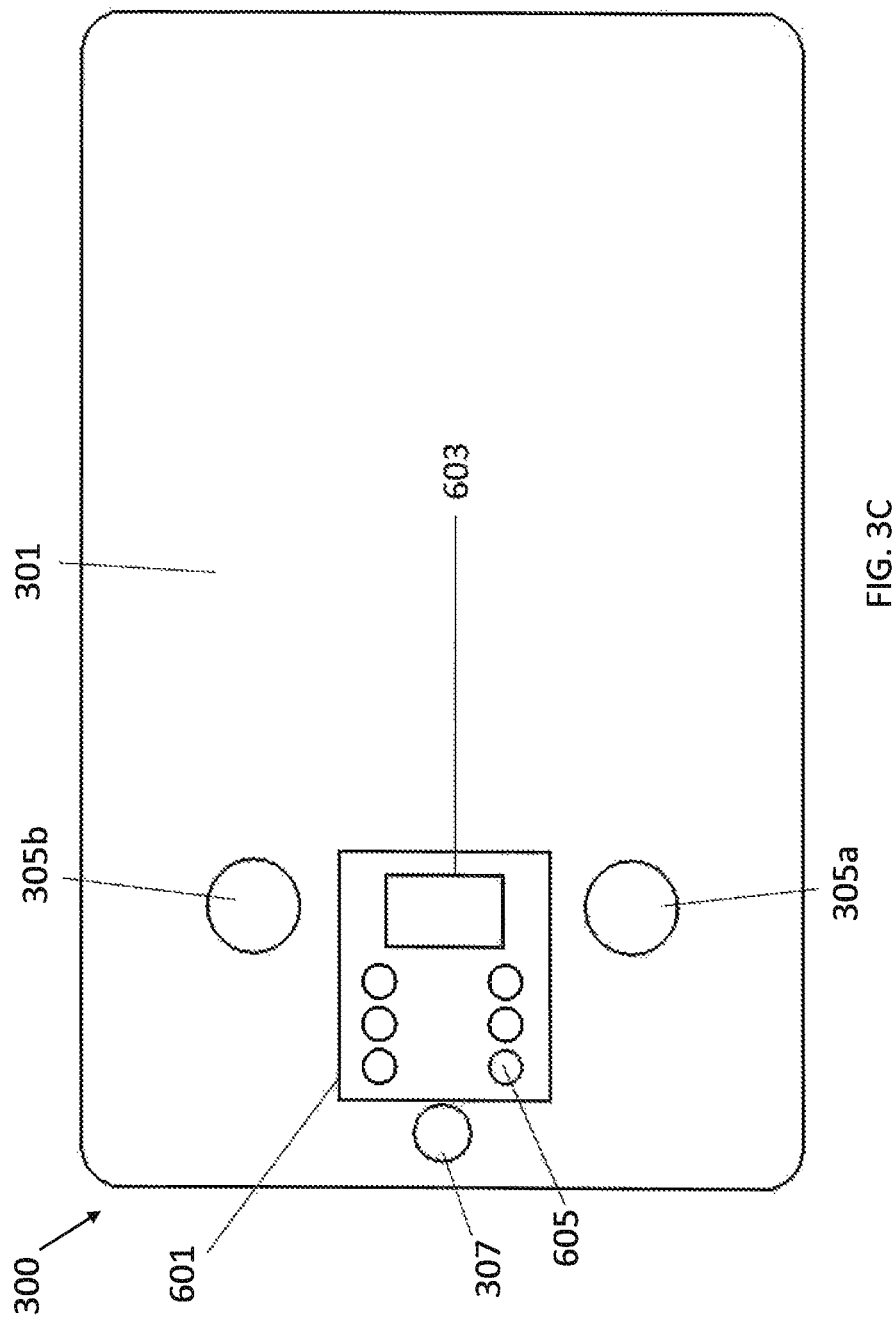
FIG. 3C is a bottom view of the plasma emitter device of FIG. 3A.

FIGS. 3A-C illustrate an example embodiment of a plasma emitter device 300 that removably attaches to the present connector (i.e., connector 200 of FIGS. 2A-B). In some embodiments, the plasma emitter device may be comprised of plasma emitter array 301 and steel (or other suitable ferritic metal) plate 303. Holes 305a, 305b, and 307 extend through both plasma emitter array 301 and steel plate 303. Steel plate 303 is attached to a top face of plasma emitter array 301, and may be attached by an adhesive material that will not electrically or magnetically interact with the operation of the plasma emitting array. Attachable plasma emitter device 300 is configured to attach to connector 200 illustrated in FIG. 2A by magnetic attraction between neodymium magnets 207 and steel plate 303. The substrate of plasma emitter array 301 is inherently thin and flexible due to its material composition. In addition to providing a means for attaching the plasma emitter array to connector 200, steel plate 303 also provides additional structural rigidity to prevent damage to the array components through over flexing. Each of the holes 305a, 305b, 307 may cooperate with a corresponding alignment peg 201a, 201b, 203 on the connector 200 so that the holes 305a, 305b, 307 align with the pegs 201a, 201b, 203 and allow the plasma emitter device 300 to attach (via magnetic interface) to the connector 200. In some embodiments, the holes 305a-b, 307 align with the pegs 201a-b, 203 only when the plasma emitter device 300 is correctly oriented with respect to the connector 200.

Figure 4:
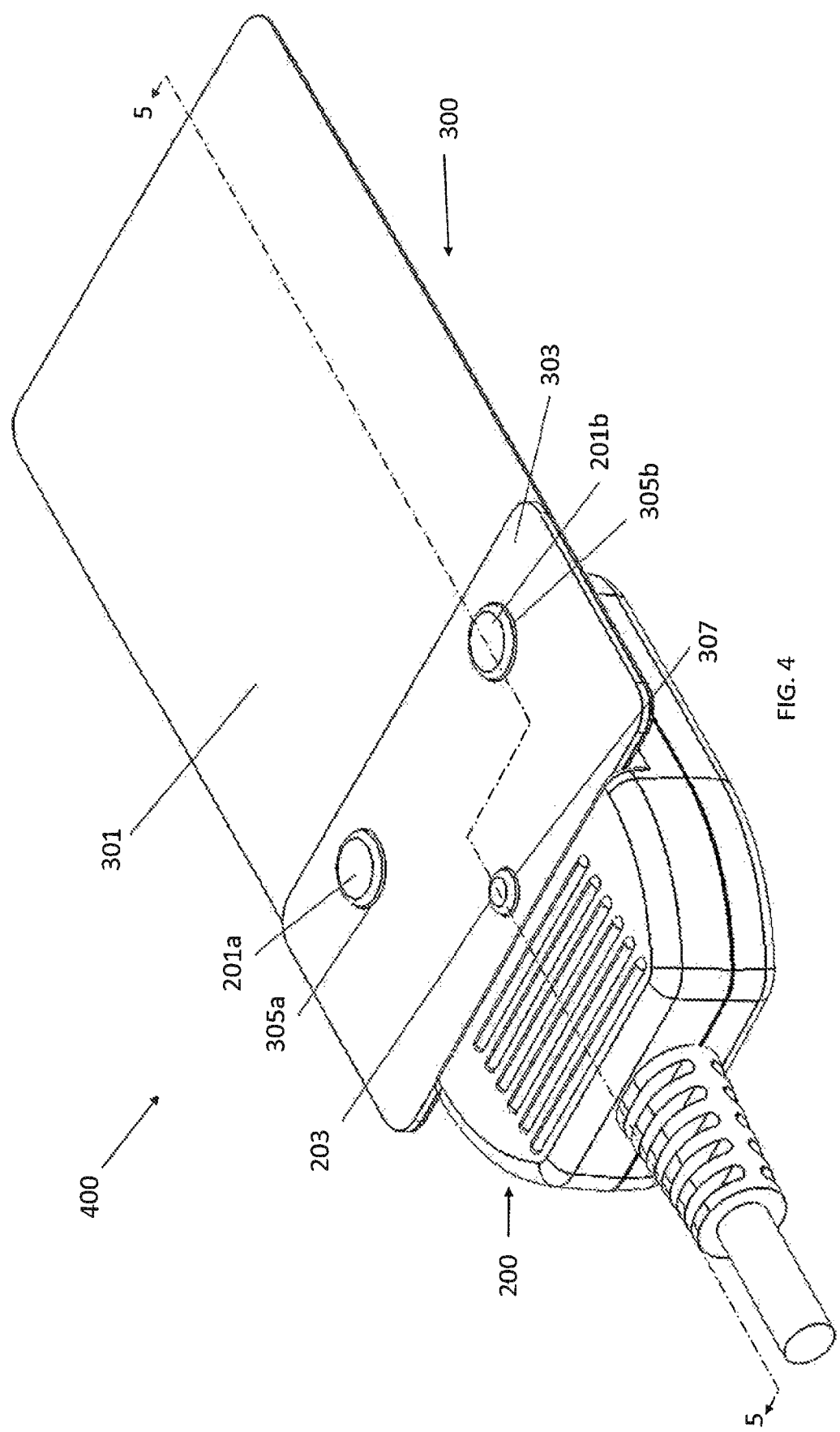
FIG. 4 is an isometric top-rear view of an example magnetic latch assembly formed between the connector of FIG. 2A and the plasma emitter device of FIG. 2A.

FIG. 3C is an illustration of the bottom surface of plasma emitter array 301 that lies coincident to connector 200. In this embodiment, the plasma emitter array 301 includes identification chip 601. The identification chip can be configured to contain a number of important information regarding patient data and non-thermal plasma parameters for therapy. Identification chip 601 may comprise a printed circuit board 603 including electronic components such as resistors, transistors, or other components that form an electric circuit. Electrical contacts 605 communicate information from identification chip 601 to an identification chip reader. When the plasma emitter device 300 and connector 200 are in the closed position, as depicted in FIG. 4, the electrical contacts 605 on identification chip 601 will align with an identification chip reader on the connector. Referring to FIG. 2A, identification chip reader 211 on connector 200 will be aligned flush with identification chip 601, such that electrical contacts 605 on identification chip 601 and electrical contacts 223 on identification chip reader 211 are in contact. Identification chip reader 211 may comprise a printed circuit board containing electronic components that electronically connect to cable 205 within the enclosed space of connector 200 and contains electronic contacts on an opposite side to interface with identification chip 601. In the closed position, the magnetic latch connector assembly device may retrieve patient information, authentication data, or plasma therapy protocols from identification chip 601 and communicate the information through the spring socket electrical contacts on identification chip reader 211 and communicate the information to a power supply controller through cable 205. Spring socket electric contacts 223 may extend upward from connector 200 to ensure good electrical contact between identification chip 601 and identification chip reader 211.

An example embodiment of plasma emitter device 300 attached to connector 200 is depicted in FIG. 4. This figure depicts an isometric view showing the top, front, and side of an example embodiment of the magnetic latch connector assembly 400. The bottom face of plasma array 301 is coincident with a top face of connector 200. Holes 305*a*, 305*b*, and 307 in plasma emitter device 300 are sized appropriately and concentrically aligned with alignment pegs 201*a*, 201*b*, and 203, respectively, on the connector 200. When the holes in device 300 are aligned with pegs on connector 200, the neodymium magnets contained within connector 200 magnetically attract steel plate 303 to removably fasten the plasma emitter device 300 to connector 200 in a closed position, with the bottom face of plasma emitter array making coincident contact with a top surface of the connector 200. In some embodiments, the alignment pegs 201*a-b*, 203 guide the plasma emitter device 300 into proper alignment for connection, so that the electrical contacts on the connector 200 establish electrical communication with the electrical contacts on the plasma emitter device 300 (see FIG. 3C).

Figure 5:
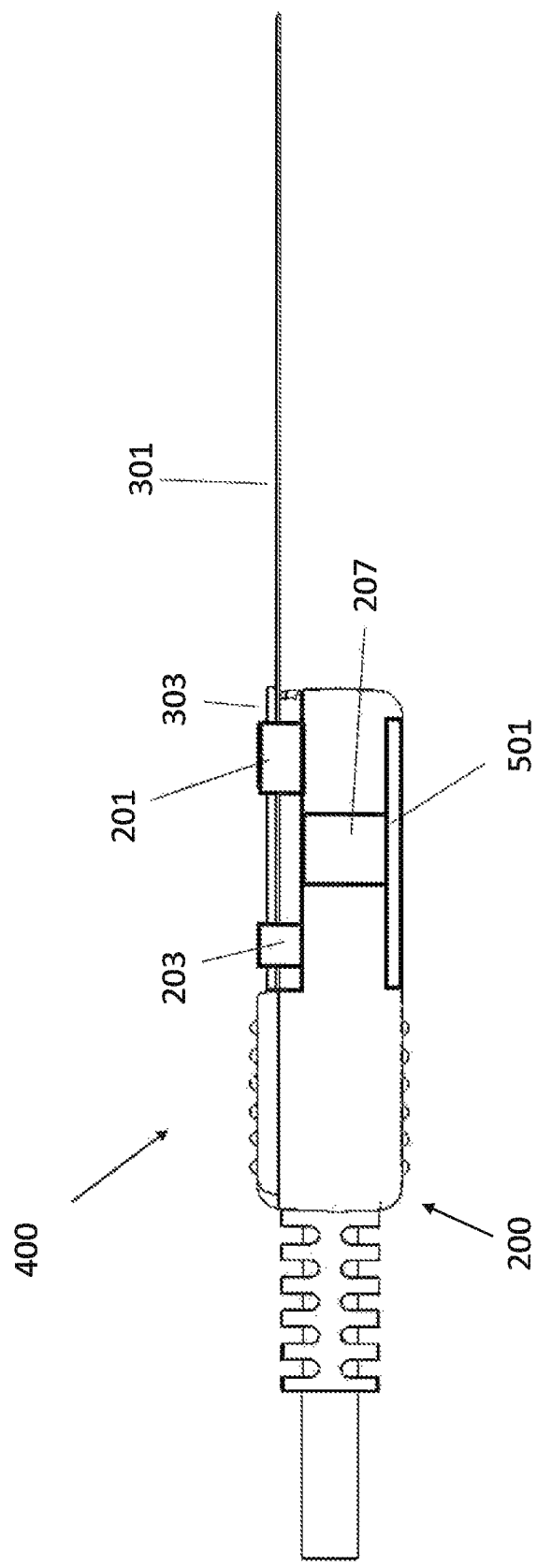
FIG. 5 is a right side cross-sectional view of the connector, plasma emitter device, and magnetic latch assembly taken along line 5-5 of FIG. 4.

FIG. 5 is an internal side view of the magnetic latch connector assembly 400 in the closed (i.e., attached) position. Steel plate 303, neodymium magnet 207, and steel plate 501 located in the enclosed space of connector 200 forms a magnetic circuit. The thickness of steel plate 303 and steel plate 501 and the arrangement of the poles of neodymium magnet 207 are configured so the magnetic circuit is self-shielding, so as not to interfere with the operation of the electronic circuit that produces the plasma or the healing process when the device is in operation.

The quick connect configuration of magnetic latch connector assembly 400 will aid in the efficiency and streamline the delivery of plasma therapies. The power supply controller is a reusable, relatively high cost device, particularly as related to a plasma array. It may be used in a clinical setting for delivering different plasma therapy protocols to a number of patients, or possibly for home use to provide plasma therapy to a single patient that exceeds the lifetime of a plasma emitter. It is contemplated that a single controller may be used by a doctor or other medical professional to deliver a number of plasma therapies throughout the course of a day.

In an example embodiment the identification feature is a chip encoded with an embedded code that acts as an authentication handshake between a plasma emitter array and connector to make sure that only authorized arrays are used with a given power supply.

The connector may communicate settings for power, modulation details and time of a desired treatment from the plasma emitter array to the power supply controller. The identification chip reader on a connector may include an identification feature that is ensures that the power supply controller is being used with an array of the appropriate size or shape for the desired treatment or patient. The power supply controller, identification chip, and identification chip reader may be configured in a number of ways to do so.

In general, a prescriber may connect an identification chip on a plasma emitting array to a computing device. A software application running on the computing device performs authentication of the plasma emitter array using the identification chip. The software application may load patient data, such as required frequency, power, or therapy duration information, and programs the "prescription" on the identification chip on the plasma emitter array. When the plasma emitter array is connected to the magnetic latch connector assembly, the identification chip reader in the connector is able to authenticate the plasma array and transmit patient data and specifications of the array, such as size and type, to the power supply controller.

Data regarding the power supply controller parameters recorded during therapeutic treatments may be transmitted through the identification chip reader on the connector to the identification chip on the plasma array for uploading to a computing device after the treatment. This data can be used post-treatment to determine efficacy and to verify that the prescription was properly applied.

In one embodiment prescribers may download prescriptions and upload treatment data from a central database rather than entering them directly. For example, a mobile computing device may be connected to an array. A central database accessible to the mobile computing device may function as a physician's prescription book which contains authentication codes registered to, for example, a physician, clinician, pharmacist or pharmacy. In this manner a prescription can be downloaded and applied to the identification chip of a plasma array. When the plasma array is then connected to a connector, the identification chip reader authenticates the array and communicates the prescription to the power supply controller. This example embodiment may enable home-use of plasma arrays for therapies, and the analogous idea of "refilling" a prescription. Alternatively, it could be used by physicians or patients in remote areas.

In another embodiment, the array will work only if the identification chip on the plasma emitter array matches the identification chip reader on the connector. For example, a programmed connector may be paired with a plasma emitter array to be given to a patient by a physician, with the patient's prescription loaded on the identification chip on the plasma emitter array. The patient then attaches the connector to a power supply controller to apply therapeutic non-thermal plasma in a home setting. In this embodiment, power supply controllers may be sold with no prescription over the counter, and preprogrammed plasma emitter arrays may be acquired with a prescription when needed. Physicians or pharmacists may then program a connector directly with customized protocols or they may program them with common protocols stored in a centralized prescription database. The identification chip reader on the connector may be programmed to record parameters of the treatment, which may be evaluated post-treatment by a physician to verify that the prescription was applied and to judge its efficacy.

Thus, in various aspects, the present specification and drawings provide a non-thermal plasma treatment device and a connector for a non-thermal plasma treatment device. The connector includes: a casing forming an interior space and including a planar receiving surface; one or more alignment pegs attached to or integral with the casing, the one or more alignment pegs extending away from the interior space and beyond the receiving surface; one or more magnets disposed substantially within the interior space and approximate the receiving surface of the casing, the one or more magnets cooperating with the one or more alignment pegs, a metal plate of a plasma emitter device, and one or more holes of the plasma emitter device to form a magnetic latch assembly having a closed position wherein the one or more magnets attract the metal plate and the one or more alignment pegs extend through the one or more holes to secure the plasma emitter device against the receiving surface of the casing; and, a first electrical contact electrically connected to a power supply of the plasma emitter device, the first electrical contact supported by the casing and extending beyond the receiving surface, the first electrical contact being in electrical communication, when the magnetic latch assembly is in the closed position, with a first corresponding contact of one or more electrical contacts disposed on the plasma emitter device, such that the connector transmits an electric current from the power supply to the plasma emitter device.

The magnetic latch assembly further may have an open position wherein the plasma emitter device is detached from the connector, the one or more magnets having a combined magnetic field of sufficient strength to maintain the magnetic latch assembly in the closed position during a treatment using the plasma treatment device, and to allow a user of the plasma treatment device to intentionally detach the plasma emitter device from the connector. The casing further may include one or more apertures disposed through the receiving surface, each magnet of the one or more magnets extending through a corresponding aperture of the one or more apertures; each magnet of the one or more magnets may include a planar top surface that is coplanar with the receiving surface. The one or more holes of the plasma emitter device may align with the one or more alignment pegs only when the plasma emitter device is correctly oriented with respect to the connector. The one or more alignment pegs may include a first alignment peg having a first size and a second alignment peg having a second size different from the first size.

The connector may further include a steel plate disposed within the interior space at an end of the one or more magnets opposite the receiving surface, the steel plate and the one or more magnets arranged to form, with the metal plate of the plasma emitter device, a magnetic circuit that is self-shielding so as not to interfere with an electronic circuit that produces plasma when the plasma treatment device is in operation. The connector may include a second electrical contact electrically connected to a controller of the plasma emitter device, the second electrical contact supported by the casing and extending beyond the receiving surface, the second electrical contact being in electrical communication, when the magnetic latch assembly is in the closed position, with a second corresponding contact of a plurality of electrical contacts, including the first corresponding contact, disposed on the plasma emitter device, such that the controller is able to read electronic information stored on the plasma emitter device.

In another aspect, the present specification and drawings provide a plasma treatment device including a connector that includes: a casing that mechanically supports a removably attachable plasma emitter device; one or more magnets disposed substantially within the casing and cooperating at least with a metal plate of the plasma emitter device to form a magnetic latch assembly having a closed position wherein the one or more magnets attract the metal plate to secure the plasma emitter device against the casing; and, an electrical interface supported by the casing and electrically connected to a power supply, the electrical interface establishing an electrical connection, when the magnetic latch assembly is in the closed position, with the plasma emitter device, such that the connector transmits an electric current generated by the power supply to the plasma emitter device. The plasma treatment device may further include a controller electrically connected to the power supply and to the electrical interface of the connector, the controller comprising a processor and memory storing computer program instructions that, when executed, cause the controller to obtain, via the electrical connection of the electrical interface to the plasma emitter device, electronic information from the plasma emitter device and perform one or more actions based on the electronic information. The one or more actions may include: determining whether the electronic information includes identifying information indicating that the plasma emitter device is an authorized device usable with the plasma treatment device; responsive to a determination that the electronic information includes the identifying information, enable a user of the plasma treatment device to perform a non-thermal plasma treatment using the plasma treatment device with the plasma emitter device attached; and, responsive to a determination that the electronic information does not include the identifying information, prevent the user of the plasma treatment device from performing the non-thermal plasma treatment using the plasma treatment device with the plasma emitter device attached. The one or more actions may further include: determining that the electronic information includes a treatment protocol describing a non-thermal plasma treatment for a first patient; and, controlling the power supply to cause the plasma emitter device to produce non-thermal plasma in accordance with the treatment protocol.

The casing may include a planar receiving surface that contacts the plasma emitter device when the magnetic latch assembly is in the closed position; a first magnet of the one or more magnets may include a planar top surface that is coplanar with the receiving surface. The casing may include one or more alignment pegs that align with one or more corresponding holes in the plasma emitter device when the plasma emitter device is correctly oriented with respect to the connector. The one or more alignment pegs may include a first alignment peg having a first size and a second alignment peg having a second size different from the first size. The casing may define an interior space substantially containing the one or more magnets, the connector further including a steel plate disposed within the interior space and cooperating with the one or more magnets and the plasma emitter device to form, when the magnetic latch assembly is in the closed position, a magnetic circuit that is self-shielding so as not to interfere with an electronic circuit that produces plasma when the plasma treatment device is in operation.

The specification and drawings are to be regarded in an illustrative rather than a restrictive sense. It will, however, be evident that various modifications and changes may be made thereunto without departing from the broader spirit and scope of the invention as set forth in the claims. Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. In addition, unless otherwise noted or contradicted by context, the term "plurality" indicates a state of being plural (e.g., "a plurality of items" indicates multiple items). The number of items in a plurality is at least two, but can be more when so indicated either explicitly or by context.

Operations/actions of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory. In some embodiments, the code is stored on set of one or more non-transitory computer-readable storage media having stored thereon executable instructions that, when executed (i.e., as a result of being executed) by one or more processors of a computer system, cause the computer system to perform operations described herein. The set of non-transitory computer-readable storage media may comprise multiple non-transitory computer-readable storage media and one or more of individual non-transitory storage media of the multiple non-transitory computer-readable storage media may lack all of the code while the multiple non-transitory computer-readable storage media collectively store all of the code. Further, in some examples, the executable instructions are executed such that different instructions are executed by different processors. As an illustrative example, a non-transitory computer-readable storage medium may store instructions. Generally, different components of a computer system may have separate processors (e.g., a main CPU and a graphics processor unit), and different processors may execute different subsets of the instructions.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described herein; variations of those embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All publications, patent applications, and patents, and the subject matter thereof, referenced herein are hereby incorporated by reference to the same extent as if each reference were individually and specifically indicated to be incorporated by reference and were set forth in its entirety herein.

What is claimed is:

1. A plasma treatment device comprising:
   a connector comprising:
   a casing that mechanically supports a removably attachable plasma emitter device;
   one or more magnets disposed within the casing and cooperating at least with a ferritic metal plate of the plasma emitter device to form a magnetic latch assembly having a closed position wherein the one or more magnets attract the metal plate to secure the plasma emitter device against the casing; and
   an electrical interface supported by the casing and electrically connected to a power supply, the electrical interface establishing an electrical connection, when the magnetic latch assembly is in the closed position, with the plasma emitter device, such that the connector transmits an electric current generated by the power supply to the plasma emitter device.

2. The plasma treatment device of claim 1, further comprising a controller electrically connected to the power supply and to the electrical interface of the connector, the controller comprising a processor and memory storing computer program instructions that, when executed, cause the controller to obtain, via the electrical connection of the electrical interface to the plasma emitter device, electronic information from the plasma emitter device and perform one or more actions based on the electronic information.

3. The plasma treatment device of claim 2, wherein the one or more actions comprise:
   determining whether the electronic information includes identifying information indicating that the plasma emitter device is an authorized device usable with the plasma treatment device;
   responsive to a determination that the electronic information includes the identifying information, enable a user of the plasma treatment device to perform a non-thermal plasma treatment using the plasma treatment device with the plasma emitter device attached; and responsive to a determination that the electronic information does not include the identifying information, prevent the user of the plasma treatment device from performing the non-thermal plasma treatment using the plasma treatment device with the plasma emitter device attached.

4. The plasma treatment device of claim 2, wherein the one or more actions comprise:
   determining that the electronic information includes a treatment protocol describing a non-thermal plasma treatment for a first patient; and
   controlling the power supply to cause the plasma emitter device to produce non-thermal plasma in accordance with the treatment protocol.

5. The plasma treatment device of claim 1, wherein the casing comprises a planar receiving surface that contacts the plasma emitter device when the magnetic latch assembly is in the closed position.

6. The plasma treatment device of claim 5, wherein a first magnet of the one or more magnets comprises a planar top surface that is coplanar with the receiving surface.

7. The plasma treatment device of claim 1, wherein the casing comprises one or more alignment pegs that align with one or more corresponding holes in the plasma emitter device when the plasma emitter device is correctly oriented with respect to the connector.

8. The plasma treatment device of claim 7, wherein the one or more alignment pegs include a first alignment peg having a first size and a second alignment peg having a second size different from the first size.

9. The plasma treatment device of claim 1, wherein the casing defines an interior space substantially containing the one or more magnets.

10. The plasma treatment device of claim 9, wherein the connector further comprises a steel plate disposed within the interior space of the casing and cooperating with the one or more magnets and the plasma emitter device to form, when the magnetic latch assembly is in the closed position, a magnetic circuit that is self-shielding so as not to interfere with an electronic circuit that produces plasma when the plasma treatment device is in operation.

11. The plasma treatment device of claim 9, wherein the casing comprises a planar receiving surface and a first magnet of the one or more magnets comprises a planar top surface that is coplanar with the receiving surface, the receiving surface and the top surface of the first magnet contacting a planar magnetic surface of the plasma emitter device when the magnetic latch assembly is in the closed position.

12. The plasma treatment device of claim 11, wherein the connector further comprises one or more alignment pegs attached to or integral with the casing, the one or more alignment pegs extending away from the interior space and beyond the receiving surface and passing through corresponding holes in the plasma emitter device to align the plasma emitter device relative to the connector when the magnetic latch assembly is in the closed position.

13. The plasma treatment device of claim 1, wherein the magnetic latch assembly further has an open position wherein the plasma emitter device is detached from the connector, the one or more magnets having a combined magnetic field of sufficient strength to maintain the magnetic latch assembly in the closed position during a treatment using the plasma treatment device, and to allow a user of the plasma treatment device to intentionally detach the plasma emitter device from the connector.

14. The plasma treatment device of claim 3, wherein the one or more actions further comprise:
   determining that the electronic information includes a treatment protocol describing a non-thermal plasma treatment for a first patient; and
   controlling the power supply to cause the plasma emitter device to produce non-thermal plasma in accordance with the treatment protocol.

\* \* \* \* \*